United States Patent [19]
Baurain et al.

[11] 4,296,105
[45] Oct. 20, 1981

[54] DERIVATIVES OF DOXORUBICINE, THEIR PREPARATION AND USE

[75] Inventors: Roger M. Baurain, Kraainem; Andre B. L. Trouet, Winksele, both of Belgium

[73] Assignee: Institut International de Pathologie Cellulaire et Moleculaire, Brussels, Belgium

[21] Appl. No.: 55,291

[22] Filed: Jul. 5, 1979

[30] Foreign Application Priority Data

Aug. 3, 1978 [BE] Belgium .................................. 869485

[51] Int. Cl.³ ........................ A61K 31/71; C07H 15/24
[52] U.S. Cl. .................................. 424/180; 536/17 A; 260/345.7 R
[58] Field of Search ................. 260/345.9 R, 345.7 R; 424/283, 253, 180; 544/271; 536/17 A

[56] References Cited

U.S. PATENT DOCUMENTS 3,665,018  5/1972  Jolles ........................... 260/345.9 R
4,012,448  3/1977  Smith et al. .................. 260/345.9 R
4,077,988  3/1978  Arcamone et al. ........... 260/345.9 R

FOREIGN PATENT DOCUMENTS 1212460  11/1970  United Kingdom ......... 260/345.7 R

Primary Examiner—Nicky Chan
Attorney, Agent, or Firm—Haseltine and Lake

[57] ABSTRACT

New derivatives of doxorubicine of the formula wherein R represents a radical of the formula $$R_1-\underset{\underset{R_2-NH}{|}}{CH}-CO- \quad (II)$$

wherein $R_1$ represents hydrogen, alkyl (possibly substituted with amino, alkylamino, dialkylamino, hydroxy, mercapto or methylthio), phenyl, benzyl (possibly substituted with one or more hydroxy) and $R_2$ represents hydrogen or forms with $R_1$ an alkylene radical, the salts thereof and pharmaceutical compositions containing said compounds.

They are prepared according to methods known in peptidic chemistry by reacting a reactive form of an aminoacid of the formula $$R_1-\underset{\underset{R_2-NH}{|}}{CH}-COOH \quad (III)$$

with doxorubicine.

7 Claims, No Drawings

DERIVATIVES OF DOXORUBICINE, THEIR PREPARATION AND USE

The present invention relates to new derivatives of doxorubicine of the general formula

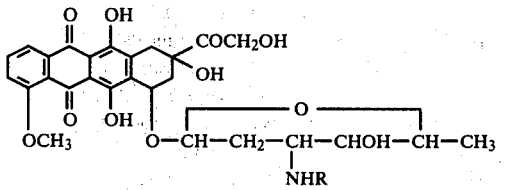

as well as their acid addition salts, the process for preparing them and pharmaceutical compositions containing said compounds.

In the general formula (I), R represents a radical of the general formula

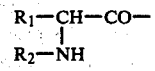

in which $R_1$ represents a hydrogen atom or an alkyl radical (possibly substituted with an amino, alkylamino, dialkylamino, hydroxy, mercapto or methylthio substituent), a phenyl radical or a benzyl radical the ring of which may carry one or two hydroxy radicals and $R_2$ represents a hydrogen atom or forms with $R_1$ an alkylene radical containing 3 or 4 carbon atoms, it being understood that each of the various radicals and alkyl moieties contains 1 to 4 carbon atoms forming a straight or branched chain and that the products of the general formula (I) may be derived from D, L or DL forms of the aminoacid acid of the general formula

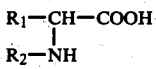

According to this invention, the new derivatives of the general formula (I) are obtained by reacting an aminoacid of the formula (III) in an activated form in which $R_1$ and $R_2$ are as defined above, with doxorubicine of the formula

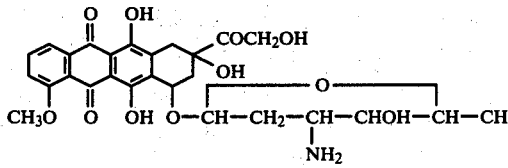

according to any of the known methods used un peptidic chemistry.

In all of these processes, it is particularly advantageous to protect the amino function and activate the carboxy group of the aminoacid of the general formula according to any of the following methods:

(a) It is for example possible to achieve simultaneously protection of the amino function and activation of the carboxy group by preparing a N-carboxyanhydride of the general formula:

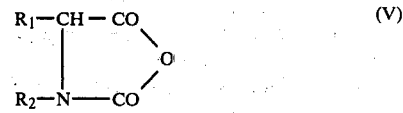

wherein $R_1$ and $R_2$ are as defined previously by causing phosgene to act upon the aminoacid of the general formula (III)

Condensation of the product of formula (IV) with the product of formula (V) generally takes place in an aqueous or hydroorganic medium which is buffered at a pH between 8 and 11, at a temperature close to 0° C.

(b) It is also feasible to protect one or more of the amino functions of the aminoacid of the formula (III) and then activate the acid function.

The protecting groups for one or more of the amino functions may if desired be eliminated later on by operations which do not affect the remainder of the molecule. Preferably the protecting group is trityl or a t-butyloxycarbonyl radical which may be eliminated in diluted acid medium.

Where the amino acid has several amino groups under determined circumstances the protectin group of the amino function in α-position with respect to the carbonyl group can be removed selectively because it can be detached easier than the protecting groups of the other amino functions.

The acid function may be activated by esterification with hydroxylated compounds such as N-hydroxysuccinimide, p-nitrophenol, 2,4,5-trichlorophenol or 4-hydroxy piperidine. Such activated ester may be prepared in situ.

Under these conditions, condensation reaction of the protected and activated aminoacid with a product of the formula (IV) takes place in a solvent such as ethyl acetate or dimethylformamide in the presence of a carbodiimide such as dicyclohexylcarbodiimide at a temperature between $-15°$ and $+25°$ C. possibly in the presence of an organic base such as triethylamine.

(c) It is also possible to condense an aminoacid of the general formula (III) possibly having one or more amino functions protected as indicated above with a product of formula (IV) in an organic solvent such as ethyl acetate, dimethylformamide, acetonitrile or methylene chloride at a temperature between 0° and 30° C. in the presence of a carbodiimide such as dicyclohexylcarbodiimide.

The starting product of formula IV is known as doxorubicine. Its preparation and physico-chemical characteristics are described in Belgian Pat. No. 731,398.

The new products prepared in accordance with the invention may be transformed if desired into acid addition salts.

Said acid addition salts can be obtained by reacting the new compounds with acids in appropriate solvents. As organic solvents one uses for example alcohols, ethers, ketones or chlorinated solvents. The salt formed precipitates, if necessary, after concentration of its solution and is separated by filtration or decantation.

The new derivatives of doxorubicine of the general formula (I) as well as their salts possess interesting antitumoral properties together with low toxicity.

They proved to be particularly active in $DBA_2$ mice affected with leukemia L1210 (subcutaneous inoculation). The tests were made with mice weighing 20 to 22 g grafted subcutaneously with $10^6$ cells of leukemia L1210 and treated with daily doses between 5 and 60 mg/kg i.v.

A preferred product is N-(L-leucyl)doxorubicine i.e. a product of formula (I) wherin R is represented by a radical of formula (II) wherein $R_1$ is isobutyl and $R_2$ is hydrogen.

The toxicity of N-(L-leucyl)doxorubicine in mice is shown by a 50% lethal dose ($LD_{50}$) of about 67 mg/kg a day (i.v. injection 2 consecutive days) i.e. 6 times more than for doxorubicine.

In $DBA_2$ mice, weighing from 20–22 g, grafted subcutaneously with $10^6$ cells of leukemia L1210 and treated i.v. (days 1 and 2), N-(L-leucyl)doxorubicine, at 48 mg/kg a day, induces 131% of increase in life span (ILS), 33% surviving animals at long term and an average tumoral volume of 0.01 mm$^3$ on day 12.

At equitoxic dose, doxorubicine induces 78% ILS, 16% of surviving animals at long term and an average tumoral volume of 24 mm$^3$ on day 12.

The following example, given in non limiting way shows how the invention should be put into practice.

EXAMPLE 50 mg of doxorubicine hydrochloride are dissolved into 1 cm$^3$ of distilled water and 9 cm$^3$ of a solution buffered at pH 10.2 are added, the composition of said solution being, for 1 liter:

boric acid: 6.184 g
potassium chloride: 7.456 g
normal soda solution: 88 cm$^3$
distilled water: up to 1 liter.

The solution is cooled to 0° C. and a solution of 0.001 mole of L-leucine carboxyanhydride in 0.5 cm$^3$ of acetone cooled to −10° C. is added. The mixture is stirred vigorously for 10 minutes at 0° C. The pH is then brought to 4 by means of 6 N sulfuric acid. After having stirred the solution at acid pH for 10 minutes, the pH is brought to 7 by addition of a normal soda solution. After lyophilisation, the powder obtained is dissolved into 10 cm$^3$ of a mixture of methanol and chloroform (50/50 by volume) and the mineral salts are then separated by filtration on 10 g of silicagel. The filtrate is evaporated to dryness under reduced pressure (25 mm of mercury) at a temperature less than 50° C. The residue is chromatographed on a column of 2 cm diameter containing 10 g of silicagel using an eluating agent consisting of a mixture of chloroform and methanol (93/7 by volume). The eluate containing N-(L-leucyl) doxorubicine is evaporated to dryness under reduced pressure (25 mm of mercury) at a temperature below 50° C. One obtains in that way 25.5 mg of N-(L-leucyl)doxorubicine as a red powder.

By dissolving said powder into an aqueous solution containing an equivalent of hydrochloric acid then lyophilizing the solution obtain, one obtains 27 mg of N-(L-leucyl)doxorubicine hydrochloride melting at 193° C. (decomp.).

For therapeutical use, the product according to the invention may be used either in its free condition or as a salt of addition with pharmaceutically acceptable acids i.e. those which are non toxic at doses applied.

As examples of addition salts with pharmaceutically acceptable acids there may be cited salts of inorganic acids such as hydrochloride, sulfate, nitrate, phosphate, or organic acids such as acetate, propionate, tartrate, theophilline-acetate, silicylate, phenolphtalinate, methylene bis-$\beta$-oxynaphtoate.

The present invention also comprises medicinal compositions containing products of formula (I) or their addition salts with acids, associated with any other pharmaceutically acceptable product be it inert or physiologically active.

These compositions may be presented in any suitable form adapted to the intended route of administration. Parenteral and more particularly intravenous route is preferred.

The compositions according to the invention for parenteral administration may be aqueous or non-aqueous sterile solutions, suspensions or emulsions. As solvent or vehicle one may use propylene glycol, vegetable oils and particularly olive oil and injectable organic esters, e.g. ethyl oleate. These compositions may also comprise adjuvants, particularly wetting, emulsifying and dispersing agents. Sterilization may be effected in various ways for example by means of a bacteriological filter, by incorporating sterilizing agents in the composition, by irradiation or by heating. They may also be prepared in the form of solid sterile compositions which can be dissolved or dispersed at the moment of use in sterile water or any other injectable sterile medium.

The products of formula (I) and their acid addition salts are used more particularly in the treatment of acute lymphoblastic and myeloblastic leukemias, lymphosarcomes, the Hodgkin disease and solid tumours (pulmonary cancer, mammary cancer, digestive tube cancer and metastases) at daily doses generally comprised between 1 and 5 mg/kg intravenously for human adult.

By way of example, a unit of composition may contain an amount of 50–100 mg of active compound.

The following example illustrates a composition according to the invention.

EXAMPLE OF COMPOSITION

One prepares a solution containing 17.39 mg/cm$^3$ of N-(L-leucyl)doxorubicine hydrochloride by dissolving 1.739 g of this product into apyrogenous physiological solute in a sufficient amount to provide 100 cm$^3$. The solution obtained is distributed aseptically in ampoules to provide 5 cm$^3$ per ampoule. The ampoules are sealed and each of them contains 80 mg of N-(L-leucyl)doxorubicine (base).

It should be understood that many modifications may be brougth by the skilled art man to the products and processes which have been described here only by way of non limiting examples without leaving the scope of the invention.

What we claim is:

1. Derivatives of doxorubicine selected from the group consisting of a compound of the formula

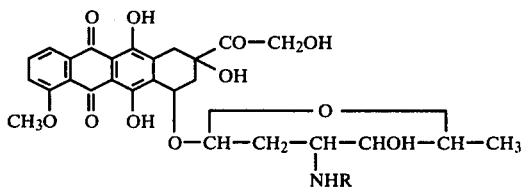

wherein R is D—, L— and DL-leucyl and the acid addition salts thereof.

2. A derivative of doxorubicine according to claim 1 wherein the acid addition salt is selected from the group consisting of the hydrochloride, sulfate, nitrate, phosphate, acetate, propionate, tartrate, theophilline-acetate, salicylate, phenolphtalinate and methylene-bis-β-oxynaphtoate salts.

3. A derivative of doxorubicine according to claim 1 wherein said compound is N-(L-leucyl)doxorubicine or an acid addition salt thereof.

4. A compound according to claim 3 which is N-(L-leucyl)-doxorubicine-hydrochloride.

5. A veterinary composition, which contains an antitumoral effective amount of N-leucyl-doxorubicine or an acid addition salt thereof together with one or more compatible and pharmaceutically acceptable diluents or additives.

6. A verterinary composition as defined in claim 5, adapted for parenteral administration.

7. A veterinary composition according to claim 5 wherein the effective amount of N-leucyl-doxorubicine is between 50 and 100 mg.

* * * * *